United States Patent
Van Der Heijden et al.

(10) Patent No.: US 8,664,423 B2
(45) Date of Patent: Mar. 4, 2014

(54) PROCESS FOR THE PREPARATION OF ACYLATED SECONDARY ALCOHOL ALKOXYLATES AND SECONDARY ALCOHOL ALKOXYLATES

(75) Inventors: Harry Van Der Heijden, Amsterdam (NL); Renata Helena Van Der Made, Amsterdam (NL); Jan Hermen Hendrik Meurs, Amsterdam (NL); Quoc An On, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 117 days.

(21) Appl. No.: 13/126,200

(22) PCT Filed: Oct. 28, 2009

(86) PCT No.: PCT/EP2009/064241
§ 371 (c)(1),
(2), (4) Date: May 24, 2011

(87) PCT Pub. No.: WO2010/049465
PCT Pub. Date: May 6, 2010

(65) Prior Publication Data
US 2011/0237817 A1  Sep. 29, 2011

(30) Foreign Application Priority Data
Oct. 29, 2008  (EP) .................................. 08167859

(51) Int. Cl.
| | | |
|---|---|---|
| C07C 41/26 | (2006.01) | |
| C07C 67/04 | (2006.01) | |
| C07C 67/26 | (2006.01) | |
| C07C 303/24 | (2006.01) | |
| C07C 69/003 | (2006.01) | |
| C07C 305/10 | (2006.01) | |
| C07C 69/14 | (2006.01) | |
| C07C 69/16 | (2006.01) | |
| C07C 67/29 | (2006.01) | |

(52) U.S. Cl.
USPC ........................................... 558/32; 560/246

(58) Field of Classification Search
None
See application file for complete search history.

(56) References Cited

U.S. PATENT DOCUMENTS

| | | | | |
|---|---|---|---|---|
| 4,098,818 | A | 7/1978 | Krummel et al. | 260/535 |
| 6,017,875 | A | 1/2000 | Kadono et al. | 510/506 |
| 2005/0240064 | A1 | 10/2005 | Weerasooriya et al. | |
| 2008/0167215 | A1 | 7/2008 | Bittner et al. | 510/505 |

FOREIGN PATENT DOCUMENTS

| | | | |
|---|---|---|---|
| EP | 0252250 | 1/1988 | |
| EP | 0424066 | 4/1991 | |
| EP | 1020422 | 7/2000 | ............. C07C 43/10 |
| GB | 1462134 | 3/1975 | ............. C07C 43/04 |
| GB | 1553561 | 7/1975 | ............. C11D 10/02 |
| WO | WO0238269 | 5/2002 | ............. B01J 31/04 |
| WO | WO2005115964 | 12/2005 | ............. C07C 67/00 |
| WO | WO2007094211 | 8/2007 | ............. C07C 67/05 |

OTHER PUBLICATIONS

Kurata, N. and Koshida, K.; "Oxidize n-paraffins for sec-alcohols"; Hydrocarbon Processing; 1978, 57(1), pp. 145-151.
Dean, Philip A, et al.; A P nmr spectroscopic study of complexation of tin(II) and lead(II) by some phosphines, phosphine oxides, and related ligands, with tetraoxides . . . ; Can. J. Chem; vol. 59; 1981.
Rabjohn, N.; "Organic Syntheses"; Collective vol. 4, ed.; John Wiley and Sons; New York, 1963; pp. 261.
Choi, Jun-Chul, et al; "Iron-Catalysed green synthesis of carboxylic esters by the intermolecular addition of carboxylic acids to alkenes"; Chem. Commun.; pp. 777-779; 2008.
Choi, Jun-Chul, et al; Supplemental Information; "Iron-Catalysed green synthesis of carboxylic esters by the intermolecular addition of carboxylic acids to alkenes"; Chem Commun.; pp. S1-S4' 2007.
Oe, Yohel et al.; "Ruthenium Catalyzed Addition Reaction of Carboxylic Acid Across Olefins Without β-hydride Elimination"; Published as Advanced Article on the Internet; www.rsc.org/chemcomm; Jun. 15, 2004.
Shell Chemicals; "Oleofins & Parafifins"; Internet Article; XP002523113; http://www.shell.com/home/content/chemicals/products_services/our_products/alpha_olefins_detergent_alcohols/neoflo/olefins_paraffins/neoflo_olefins_paraffins.html; Apr. 8, 2009.

*Primary Examiner* — Sun Jae Loewe

(57) ABSTRACT

A process for the preparation of acylated secondary alcohol alkoxylates and a process for making secondary alcohol alkoxy sulfates comprising the steps of:—
preparing secondary alcohol alkoxylates by the afore-mentioned process; and
sulfating the secondary alcohol alkoxylates is described.

17 Claims, No Drawings

PROCESS FOR THE PREPARATION OF ACYLATED SECONDARY ALCOHOL ALKOXYLATES AND SECONDARY ALCOHOL ALKOXYLATES

PRIORITY CLAIM

The present application claims priority from PCT/EP2009/064241, filed 28 Oct. 2009, which claims priority from European Application EP 08167859.1, filed 29 Oct. 2008.

FIELD OF THE INVENTION

The present invention relates to a process for the preparation of acylated secondary alcohol alkoxylates and secondary alcohol alkoxylates.

BACKGROUND OF THE INVENTION

A large variety of products useful, for instance, as non-ionic surfactants, wetting and emulsifying agents, solvents and chemical intermediates are prepared by the addition reaction (alkoxylation reaction) of alkylene oxides (epoxides) with organic compounds having one or more active hydrogen atoms.

For example, alcohol ethoxylates may be prepared by the reaction of ethylene oxide with aliphatic alcohols of 6 to 30 carbon atoms. Such ethoxylates, and to a lesser extent the corresponding propoxylates and compounds containing mixed oxyethylene and oxypropylene groups, are widely employed as non-ionic detergent components in cleaning and personal care formulations.

US 2008/0167215 A1 discloses specific acylated alcohol alkoxylates for use as low-foam surfactants.

Sulphated alcohol alkoxylates have a wide variety of uses as well, especially as anionic surfactants. Sulphated higher secondary alcohol ethoxylates (SAES) offer comparable properties in bulk applications relative to anionic surfactants such as linear alkyl benzene sulphonates and primary alcohol ethoxy sulphates, as well as methyl ester sulphonates. These materials may be used to produce household detergents including laundry powders, laundry liquids, dishwashing liquids and other household cleaners, as well as lubricants and personal care compositions and as surfactants for (dilute) surfactant flooding of oil wells and as surfactant components used in e.g. alkali, surfactants and polymer containing mixtures, suitable for enhanced oil recovery.

One typical method of preparing alkoxylated alcohols, for example linear or branched primary alcohol alkoxylates, is by hydroformylating an olefin into an oxo-alcohol, followed by alkoxylation of the resulting alcohol by reaction with a suitable alkylene oxide such as ethylene oxide or propylene oxide. However, methods involving hydroformylation are expensive and hydroformylation gives rise to linear or branched primary alcohols (depending on the kind of oxo-reaction) which are to be alkoxylated subsequently.

For some applications, mixtures of secondary alcohol alkoxylates may give improved performance (for example in enhanced oil recovery (EOR) applications in relation to oil solubility).

Secondary alcohol alkoxylates are generally prepared by oxidation/hydroxylation of paraffins, e.g. by the Bashkirov reaction, followed by an alkoxylation reaction.

However, the oxidation of paraffins to secondary alcohols and their subsequent alkoxylation typically involves a complicated two-step process and is hence, an expensive route.

Said process comprises producing secondary alcohols directly from paraffins by oxidation using boric acid as a catalyst. Strictly speaking, the boron reagent is not a catalyst as it is consumed in the reaction. Its function is to protect the oxygenate (sec-alcohol) by reaction to give an oxidation-resistant borate ester. In the overall process including boric acid recycles the boric acid does act as a "catalyst" because its secondary function is to increase the oxidation rate. The borate esters of the secondary alcohols are formed and may be separated from the paraffins by distillation when the carbon number (number of carbon atoms in the alcohol chain) of the alcohol is 14 or less. However, when the carbon number is 15 or more, the distillation temperature required is equal to or above the decomposition temperature of the borate ester and therefore conventional distillation techniques may not be effective.

Furthermore, the oxidation of paraffins in the presence of boric acid derivatives leads to the formation of diols as one of the main by-products (see N. Kurata and K. Koshida, Hydrocarbon Processing, 1978, 57(1), 145-151 and N. J. Stevens and J. R. Livingston, Chem. Eng. Progress, 1968, 64(7), 61-66). Therefore one has to expect that only after very complete purification from these contaminating diols will secondary alcohols be suitable for alkoxylation and that the cost of such purification may render the economics of the overall process unviable.

An alternative route to secondary alcohol alkoxylates described in U.S. Pat. No. 6,017,875 A is by the acid-catalysed addition of oligoethylene glycol to internal olefins. However, said route is cumbersome as it also affords di-alkylated oligoalkylene glycols and internal olefin oligomers as by-products. Thus, said route is also costly.

In current industrial practice, secondary alcohol ethoxylates are made by an expensive two-step process. Firstly, two to three ethyleneoxy units are added to the secondary alcohol using (Lewis) acid catalysts to make a primary hydroxyl-containing low molecular weight (low-mol) ethoxylate. Secondly, after removal of the acid catalyst (generally by neutralisation), the desired additional amount of ethyleneoxy units is reacted with the low-molecular weight ethoxylate (predominantly a primary alcohol mixture) using a basic catalyst such as potassium hydroxide. This two-step approach has the advantage that the inevitable by-product of the (Lewis) acid catalysed ethoxylation, 1,4-dioxane, can be removed by efficient flashing or stripping after removal or by neutralisation of the acid catalyst from the low-molecular weight ethoxylate intermediate product before its conversion to the end-product with the desired level of ethoxylation.

However, it would be desirable to develop a simple and cost-effective method to produce secondary alcohol alkoxylates without 1,4-dioxane formation and without the formation of an alkoxylate with a very wide alkoxylate distribution.

In this regard, it should be noted that alkylene oxide addition reactions are known to produce a product mixture of various alkoxylate groups having different numbers of alkylene oxide adducts (oxyalkylene adducts). The adduct number is a factor which in many respects controls the properties of the alkoxylate molecule, and efforts are made to tailor the average adduct number of a product and/or the distribution of adduct numbers within a product to the product's intended service.

Alkoxylate mixtures in which a relatively large proportion of the alkoxylate molecules have a number (n) of alkylene oxide adducts that is within a relatively narrow range of values have been reported in the art as being preferred for use in certain detergent formulations (GB-A-1462134; Research Disclosure No. 194010). Narrow-range alkoxylates are also known to be particularly valuable as chemical intermediates in the synthesis of certain carboxyalkylated alkyl polyethers (U.S. Pat. No. 4,098,818) and of certain alkyl ether sulfates (GB-A-1553561).

Hence, it would be advantageous to devise an alternative method to produce secondary alcohol alkoxylates, and in particular narrow range alcohol alkoxylates, that would not only avoid having to apply hydroformylation but would also avoid having to resort to rather unstable secondary alcohols as intermediates (which may re-form internal olefins).

SUMMARY OF THE INVENTION

Accordingly, the present invention provides a process for the preparation of acylated secondary alcohol alkoxylates, said process comprising:—

(i) reaction of one or more internal olefins with one or more carboxylic acids in the presence of a catalyst composition in order to form one or more carboxylic acid esters;

(ii) reaction of one or more carboxylic acid esters from step (i) with one or more alkylene oxide reactants, in the presence of a catalytically effective amount of a catalyst composition comprising:—

(a) one or more alkaline earth metal salts of carboxylic and/or hydroxycarboxylic acids and/or hydrates of the former;

(b) an oxy-acid selected from sulphuric acid and orthophosphoric acid;

(c) an alcohol and/or an ester;

and/or products of the reciprocal reactions of (a), (b) and/or (c)

in order to form one or more acylated secondary alcohol alkoxylates.

DETAILED DESCRIPTION OF THE INVENTION

Step (i) of the process of the present invention comprises reaction of one or more internal olefins with one or more carboxylic acids in the presence of a catalyst composition in order to form one or more carboxylic acid esters.

Said internal olefins are preferably selected from olefins having in the range of from 8 to 32 carbon atoms, more preferably in the range of from 10 to 28 carbon atoms and most preferably in the range of from 12 to 24 carbon atoms.

The internal olefins used in step (i) of the process of the present invention may be substituted or unsubstituted aliphatic internal olefins.

The substituent groups in the substituted aliphatic internal olefins are not especially limited and may include substituents selected from phenyl groups, 1-naphthyl groups, 2-naphthyl groups, pyridyl groups, nitro groups, amino groups, amido groups, halogen atoms, carboxyl groups, alkoxy groups (for example, methoxy groups, ethoxy groups, phenoxy groups), aralkyl groups and heterocyclic groups.

Examples of internal olefins that may be conveniently used in the process of the present invention include internal olefin mixtures emerging from the isomerisation-disproportionation (ID) section of the Shell Higher Olefin Process (SHOP), optionally after passing over the olefins isomerisation unit (OIU) to increase the branching level of the largely linear internal olefins of the ID section to approximately one alkylbranch per chain, e.g. internal $C_8$-$C_{10}$ olefin mixtures, internal $C_{10}$ olefins, internal $C_{11}$-$C_{12}$ olefin mixtures, internal $C_{11}$-$C_{14}$ olefin mixtures, internal $C_{15}$-$C_{16}$ olefin mixtures and internal $C_{15}$-$C_{18}$ olefin mixtures. Examples of internal olefins that may be conveniently used in the process of the present invention also include internal olefin mixtures produced by UOP's paraffin conversion (PACOL) process on paraffin streams emerging from the gas-to-liquids (GTL) process or from refinery de-waxing processes. Furthermore, olefin mixtures directly emerging from Fischer-Tropsch route to paraffins, olefins and oxygenates may also be conveniently employed in the process of the present invention.

Carboxylic acids that may be conveniently used in step (i) of the process of the present invention are not limited. Said carboxylic acids may be optionally substituted with one or more inert functional groups, that is to say functional groups that will not interfere to in the reaction of step (i). Examples of inert functional groups that may be present include chlorine and bromine atoms, nitro groups and alkoxy groups such as methoxy groups.

Preferably, said carboxylic acids may be selected from branched and unbranched carboxylic acids having in the range of from 2 to 18 carbon atoms, more preferably in the range of from 2 to 12 and even more preferably in the range of from 2 to 8 carbon atoms.

Examples of aliphatic carboxylic acids that may be conveniently used include acetic acid, propionic acid, butyric acid and isobutyric acid.

Examples of aromatic carboxylic acids that may be conveniently used include benzoic acid, anisic acid, phenylacetic acid, o-toluic acid, phthalic acid, isophthalic acid, and terephthalic acid.

The reaction of olefins and carboxylic acids is known in the art, for example in "*Organic Syntheses*", *Collective Volume* 4, ed. N. Rabjohn, John Wiley and Sons, New York, 1963, pp. 261 and in Chem. Commun. 2004, pp. 1620. Typical methods to produce carboxylic esters from olefins include using sulphuric acid as a catalyst and the use of various metal compounds, such as those comprising metals selected from copper, silver, gold and ruthenium. *Chem. Commun.*, 2008, pp. 777-779 describes a number of methods to produce carboxylic esters from olefins. The reaction of step (i) is not limited and any method known in the art may be conveniently used.

However, in a preferred embodiment of the present invention, step (i) may be carried out in accordance with the method described in WO-A-2007/094211. That is to say, in a preferred embodiment of the present invention, the catalyst composition used in step (i) comprises (a) at least one metal compound, wherein said metal is selected from iron, cobalt and nickel; and (b) an acidic compound.

The metal compound (a) in said catalyst composition is not limited and may be conveniently selected, for example, from compounds having general formulae $FeX_n$ (wherein n is 2 or 3), $Fe(CO)_5$, $Fe_3(CO)_{12}$, $Fe(CO)_3(EN)$, $Fe(CO)_3(DE)$, $Fe(DE)_2$, $CpFeX(CO)_2$, $[CpFe(CO)_2]_2$, $[Cp*Fe(CO)_2]_2$, $Fe(acac)_3$, $Fe(OAc)_n$ (wherein n is 2 or 3), $CoX_2$, $Co_2(CO)_8$, $Co(acac)_n$ (wherein n is 2 or 3), $Co(OAc)_2$, $CpCo(CO)_2$, $Cp*Co(CO)_2$, $NiX_2$, $Ni(CO)_4$, $Ni(DE)_2$, $Ni(acac)_2$ and $Ni(OAc)_2$.

In the afore-mentioned formulae, X denotes a hydrogen atom, a halogen atom, preferably chlorine, a hydroxyl group, a cyano group, an alkoxy group, a carboxylate group or a thiocyanate group, Cp denotes a cyclopentadiene group, acac denotes an acetylacetonate group, DE denotes norbornadiene, 1,5-cyclooctadiene or 1,5-hexadiene, EN denotes ethylene or cyclooctene, and OAc denotes an acetate group.

The metal compounds (a) preferred for use in the catalyst composition of step (i) of the process of the present invention are iron compounds. Iron chloride is especially preferred for use in the catalyst composition of step (i) of the process of the present invention.

The acidic compound (b) for use in the catalyst composition of step (i) of the process of the present invention is preferably selected from a Brønsted acid or a metal salt of trifluoromethanesulphonic acid.

Whilst there is no particular limitation on the acidic compound (ii), preferred Brønsted acids include HCl, $H_2SO_4$, $CF_3SO_3H$, p-$[CH_3(CH_2)_{11}]$ $(C_6H_4)$ $SO_3H$ and acid sold under the trade designation "NAFION" from E.I. du Pont de Nemours & Co., Inc.).

Examples of metal salts of trifluoromethanesulphonic acid that may be conveniently used include $Na(OSO_2CF_3)$, $Li(OSO_2CF_3)$, $Ag(OSO_2CF_3)$, $Cu(OSO_2CF_3)_2$, $Zn(OSO_2CF_3)_2$, $La(OSO_2CF_3)_3$ and $Sc(OSO_2CF_3)_3$.

The Brønsted acid preferred for use in the catalyst composition of step (i) of the process of the present invention is trifluoromethanesulphonic acid, and the preferred metal salt of trifluoromethanesulphonic acid for use in the catalyst composition of step (i) of the process of the present invention is the silver salt of trifluoromethanesulphonic acid.

The amount of acidic compound (b) used in the catalyst composition of step (i) of the process of the present invention is not specially limited, but the amount of said acidic compound relative to the metal compound (a) is preferably in the range of from 1/300 to 10 and more preferably in the range of from 1/50 to 3, as a molar ratio.

The catalyst for use in step (i) of the process of the present invention, is preferably a combination of the afore-mentioned metal compound (a) and acidic compound (b). However, in one embodiment, the metal compound (a) and acidic compound (b) may each be prepared separately and added to the reaction mixture of step (i). Alternatively, as described in *Chem. Commun.*, 2008, pp 777-779, the metal compound (a) and acidic compound (b) may also be reacted in advance outside of the reaction mixture of step (i), in order that, for example, a metal salt of trifluoromethanesulphonic acid may be used. Examples of such salts include $Fe(OSO_2CF_3)_3$, which may be prepared by the method described in *Can. J. Chem.*, 1981, 59, 669-678.

The reaction conditions for step (i) of the process of the present invention are not limited. However, in a preferred embodiment of the present invention, step (i) may be carried out at a reaction temperature in the range of from 20 to 300° C., and more preferably at a reaction temperature in the range of from 60 to 200° C.

The reaction of step (i) of the process of the present invention may be carried out in the presence of one or more inert solvents, that is to say, solvents which do not interfere with the reaction of step (i). Alternatively, said reaction may be carried out in the absence of solvents.

Inert solvents that may be conveniently used in step (i) of the process of the present invention include, for example, hydrocarbons and ethers, more specifically, benzene, toluene, hexane, tetrahydrofuran, diethyl ether, dibutyl ether and dioxane.

Step (ii) of the process of the present invention comprises reaction of one or more carboxylic acid esters from step (i) with one or more alkylene oxide reactants, in the presence of a catalytically effective amount of a catalyst composition comprising (a) one or more alkaline earth metal salts of carboxylic and/or hydroxycarboxylic acids and/or hydrates of the former, (b) an oxy-acid selected from sulphuric acid and ortho-phosphoric acid, (c) an alcohol and/or an ester, and/or products of the reciprocal reactions of (a), (b) and/or (c) in order to form one or more acylated alcohol alkoxylates.

The catalyst composition for use in step (ii) of the process of the present invention may be prepared in accordance with the method described in WO-A-02/38269. Said catalyst composition is preferably in the form of a visually homogeneous, liquid suspension or a homogeneous paste.

Said catalyst composition preferably comprises the one or more alkaline earth metal salts of carboxylic and/or hydroxycarboxylic acids and/or hydrates of the former, and the oxy-acid selected from sulphuric acid and ortho-phosphoric acid in a total concentration in the range of from 10 to 65% by weight (wt. %), based on the total weight of said catalyst composition.

When the catalyst composition used in step (ii) comprises components (a)-(c) only and/or products of the reciprocal reactions of (a), (b) and/or (c), then it is more preferred that said components are present in amount in the range of from 16 to 26 wt. % for (a), 4 to 7 wt. % for (b), and 67 to 80 wt. % for (c), each based on the total weight of the catalyst composition.

It will be appreciated that the exact amounts of components (a)-(c) are selected from the above ranges such that the amounts thereof total 100 wt. %.

The afore-mentioned catalyst composition may be obtained as a concentrate in the form of a visually homogeneous liquid or paste by homogenisation of the so-called active ingredients (a) and (b) of the catalyst composition, prior to introducing said homogenised mixture to alcohols or esters (c), the said active ingredients being partially or entirely insoluble in the alcohols or esters used for making the catalyst concentrate as well as in the carboxylic acid ester reactants subjected to alkoxylation in step (ii).

However, whilst the carboxylic acid esters of step (i) of the process of the present invention can be efficiently alkoxylated in step (ii) of the process of the present invention using the afore-mentioned catalysts and reaction conditions according to WO-A-02/038269 and WO-A-2005/115964, the resulting acylated alcohol alkoxylates, in particular methyl ester ethoxylates (MEE) may display distinct discolouration and in particular, yellowing.

Accordingly, in a preferred embodiment of the present invention, that catalyst composition for use in step (ii) may be modified in order to surprisingly produce acylated alcohol alkoxylates additionally having advantageous colour properties, that is to say, without any substantial discolouration. Such advantageous colour properties considerably increase flexibility in the detergents industry, which generally aims to produce water-white (colourless) liquid detergent formulations or white detergent powder formulations.

Hence, it is particularly preferred that the catalyst composition for use in step (ii) of the process of the present invention comprises (a) one or more alkaline earth metal salts of carboxylic and/or hydroxycarboxylic acids and/or hydrates of the former, (b) an oxy-acid selected from sulphuric acid and ortho-phosphoric acid, (c) an alcohol and/or an ester, (d) a peroxy acid and/or a salt thereof, and/or products of the reciprocal reactions of (a), (b), (c) and/or (d).

Said catalyst composition surprisingly allows for the production in step (ii) of acylated alcohol alkoxylates, preferably fatty ester alkoxylates and more preferably narrow range fatty ester alkoxylates, for optional subsequent hydrolysis or transesterification (also known as transacylation), in step (iii), which acylated alcohol alkoxylates have advantageous colour properties, in particular having reduced yellowing.

In said preferred embodiment, wherein said catalyst composition comprises components (a)-(d) and/or products of the reciprocal reactions of (a), (b), (c) and/or (d), then it is preferred that said composition comprises:—

(a) one or more alkaline earth metal salts of carboxylic and/or hydroxycarboxylic acids and/or hydrates of the former in an amount in the range of from 8 to 53 wt. % more preferably in the range of from 16 to 26 wt. %, based on the total weight of the catalyst composition;

(b) an oxy-acid selected from sulphuric acid and orthophosphoric acid in an amount in the range of from 2 to 13 wt. %, more preferably in the range of from 4 to 7 wt. %, based on the total weight of the catalyst composition;

(c) an alcohol and/or an ester in an amount in the range of from 34 to 90 wt. %, more preferably in the range of from 67 to 80 wt. %, based on the total weight of the catalyst composition; and (d) a peroxy acid and/or a salt thereof in an amount in the range of from 10 to 10000 ppm (wt./wt.), more preferably in the range of from 30 to 3000 ppm (wt./wt.) and most preferably in the range of from 100 to 1000 ppm (wt./wt.), based on the total weight of the catalyst composition and/or products of the reciprocal reactions of (a), (b), (c) and/or (d).

It will be appreciated that the exact amounts of components (a)-(d) are selected from the above ranges such that the amounts thereof total 100 wt. %.

Alkaline earth metal salts (a) that may be conveniently used in the catalyst composition of step (ii) of the process of the present invention include calcium and magnesium salts of carboxylic and/or hydroxycarboxylic acids and/or hydrates of the former.

When the alkaline earth metal salts (a) are salts of carboxylic acids, it is particularly preferred that said salts are derived from the same one or more carboxylic acids as used in step (i) of the process of the present invention.

Salts that may be conveniently used as component (a) in the catalyst composition of step (ii) of the process of the present invention are salts of low molecular weight carboxylic acids and/or hydroxycarboxylic acids, that is to say, carboxylic acids and/or hydroxycarboxylic acids having in the range of from 1 to 18 carbon atoms.

Preferred salts are salts of carboxylic acids having in the range of from 1 to 7 carbon atoms and/or salts of hydroxycarboxylic acids having in the range of from 2 to 7 carbon atoms.

More preferred salts are salts of carboxylic acids having in the range of from 2 to 4 carbon atoms and/or salts of hydroxycarboxylic acids having in the range of from 2 to 4 carbon atoms.

Examples of salts that may be used as component (a) in the catalyst composition of step (ii) of the process of the present invention include salts of formic acid, acetic acid, propionic acid, lactic acid, isobutyric acid, 2-hydroxy-2-methylpropanoic acid and benzoic acid.

Calcium salts of carboxylic and/or hydroxycarboxylic acids having in the range of from 1 to 18 carbon atoms, preferably in the range of from 1 to 7 carbon atoms, more preferably in the range of from 2 to 4 carbon atoms, and/or hydrates of the former are preferred.

Examples of such calcium salts include calcium acetate and/or calcium lactate and/or hydrates of the former.

Specific examples of oxy-acids that may be used are concentrated (85%) ortho-phosphoric acid and concentrated (95-97%) sulphuric acid.

The alcohol which may be used as component (c) in the catalyst composition of step (ii) of the process of the present invention may be a primary, secondary or tertiary alcohol.

The alcohol and/or an ester used as component (c) in the catalyst composition of step (ii) of the process of the present invention is preferably an alcohol having in the range of from 1 to 6 carbon atoms and/or a carboxylic acid ester having in the range of from 2 to 39 carbon atoms. In a particularly preferred embodiment of the present invention, the ester component (c) may be alkoxylated.

Examples of alcohols and esters that may be conveniently used as component (c) in the catalyst composition of step (ii) of the process of the present invention include methanol, ethanol, propanol, 2-propanol (isopropyl alcohol), butanol, 2-butanol (sec-butyl alcohol) and 2-methyl-2-propanol (tert-butyl alcohol), pentanol, 2-pentanol, 3-pentanol, 3-methyl-1-butanol (isoamyl alcohol), 2,2-dimethyl-1-propanol (neopentyl alcohol), 2-methyl-2-butanol (tert-amyl alcohol), hexanol, 2-hexanol, 3-hexanol, methyl formate, ethyl formate, propyl formate, isopropyl formate, butyl formate, sec-butyl formate, isobutyl formate, pentyl formate, isoamyl formate, hexyl formate, cyclohexyl formate, heptyl formate, benzyl formate, octyl formate, nonyl formate, 1-decyl formate, the formic acid esters of sec-decyl alcohols, such as 2-decanol, 3-decanol, 4-decanol and 5-decanol and their mixtures, the formic acid esters of a mixture of sec-undecyl alcohols and sec-dodecyl alcohols, 1-dodecyl formate, formic acid esters of sec-dodecyl alcohols, such as 2-dodecanol, 3-dodecanol, 4-dodecanol, 5-dodecanol and 6-dodecanol and their mixtures, formic acid esters of a mixture of sec-tridecyl alcohols and sec-tetradecyl alcohols, the formic acid esters of a mixture of linear or branched sec-pentadecyl alcohols and sec-hexadecyl alcohols or a mixture of linear or branched sec-pentadecyl alcohols, sec-hexadecyl alcohols, sec-heptadecyl alcohols and sec-octadecyl alcohols, formic acid esters of a mixture of sec-nonadecyl alcohols, sec-eicosyl alcohols, sec-heneicosyl alcohols, sec-docosyl alcohols, sec-tricosyl alcohols, sec-tetracosyl alcohols, sec-pentacosyl alcohols, sec-hexacosyl alcohols, sec-heptacosyl alcohols, sec-octacosyl alcohols, sec-nonacosyl alcohols, sec-triacontyl alcohols, sec-hentriacontyl alcohols or sec-dotriacontyl alcohols, methyl acetate, ethyl acetate, propyl acetate, isopropyl acetate, butyl acetate, sec-butyl acetate, isobutyl acetate, tert-butyl acetate, pentyl acetate, 2-pentyl acetate, 3-pentyl acetate, isoamyl acetate, tert-amyl acetate, hexyl acetate, cyclohexyl acetate, heptyl acetate, benzyl acetate, octyl acetate, nonyl acetate, decyl acetate, the acetic acid esters of sec-decyl alcohols, such as 2-decanol, 3-decanol, 4-decanol and 5-decanol and their mixtures, the acetic acid esters of a mixture of sec-undecyl alcohols and sec-dodecyl alcohols, 1-dodecyl acetate, acetic acid esters of sec-dodecyl alcohols, such as 2-dodecanol, 3-dodecanol, 4-dodecanol, 5-dodecanol and 6-dodecanol and their mixtures, acetic acid esters of a mixture of sec-tridecyl alcohols and sec-tetradecyl alcohols, the acetic acid esters of a mixture of linear or branched sec-pentadecyl alcohols and sec-hexadecyl alcohols or a mixture of linear or branched sec-pentadecyl alcohols, sec-hexadecyl alcohols, sec-heptadecyl alcohols and sec-octadecyl alcohols, acetic acid esters of a mixture of sec-nonadecyl alcohols, sec-eicosyl alcohols, sec-heneicosyl alcohols, sec-docosyl alcohols, sec-tricosyl alcohols, sec-tetracosyl alcohols, sec-pentacosyl alcohols, sec-hexacosyl alcohols, sec-heptacosyl alcohols, sec-octacosyl alcohols, sec-nonacosyl alcohols, sec-triacontyl alcohols, sec-hentriacontyl alcohols or sec-dotriacontyl alcohols, methyl isobutyrate, ethyl isobutyrate, propyl isobutyrate, isopropyl isobutyrate, butyl isobutyrate, sec-butyl isobutyrate, isobutyl isobutyrate, tert-butyl isobutyrate, pentyl isobutyrate, 2-pentyl isobutyrate, 3-pentyl isobutyrate, isoamyl isobutyrate, tert-amyl isobutyrate, hexyl isobutyrate, cyclohexyl isobutyrate, heptyl isobutyrate, benzyl isobutyrate, octyl isobutyrate, nonyl isobutyrate, decyl isobutyrate, the isobutyric acid esters of sec-decyl alcohols, such as 2-decanol, 3-decanol, 4-decanol and 5-decanol and their mixtures, the isobutyric acid esters of a mixture of sec-undecyl alcohols and sec-dodecyl alcohols, 1-dodecyl isobutyrate, isobutyric acid esters of sec-dodecyl alcohols, such as 2-dodecanol, 3-dodecanol, 4-dodecanol, 5-dodecanol and 6-dodecanol and their mixtures, isobutyric acid esters of a mixture of sec-tridecyl alcohols and sec-tetradecyl alcohols, the isobutyric acid esters of a mixture of linear or branched sec-pentadecyl alcohols and sec-hexadecyl alcohols or a mixture of linear or branched sec-pentadecyl alcohols, sec-hexadecyl alcohols, sec-heptadecyl alcohols and sec-octadecyl alcohols, isobutyric acid esters of a mixture of sec-nonadecyl alcohols, sec-eicosyl alcohols, sec-heneicosyl alcohols, sec-docosyl alcohols, sec-tricosyl alcohols, sec-tetracosyl alcohols, sec-pentacosyl alcohols, sec-hexacosyl alcohols, sec-heptacosyl alcohols, sec-octacosyl alcohols, sec-nonacosyl alcohols, sec-triacontyl alcohols, sec-hentriacontyl alcohols or sec-dotriacontyl alcohols, methyl benzoate, ethyl benzoate, propyl benzoate, isopropyl benzoate, butyl benzoate, sec-butyl benzoate, isobutyl benzoate, tert-butyl benzoate, pentyl benzoate, 2-pentyl benzoate, 3-pentyl benzoate, isoamyl benzoate, tert-amyl benzoate, hexyl benzoate, cyclohexyl benzoate, heptyl benzoate, benzyl benzoate, octyl benzoate, nonyl benzoate, decyl benzoate, the benzoic acid esters of sec-decyl alcohols, such as 2-decanol, 3-decanol, 4-decanol and 5-decanol and their mixtures, the benzoic acid esters of a mixture of sec-undecyl alcohols and sec-dodecyl alcohols, 1-dodecyl benzoate, benzoic acid esters of sec-dodecyl alcohols, such as 2-dodecanol, 3-dodecanol, 4-dodecanol, 5-dodecanol and 6-dodecanol and their mixtures, benzoic acid esters of a mixture of sec-tridecyl alcohols and sec-tetradecyl alcohols, the benzoic acid esters of a mixture of linear or branched sec-pentadecyl alcohols and sec-hexadecyl alcohols or a mixture of linear or branched sec-pentadecyl alcohols, sec-hexadecyl alcohols, sec-heptadecyl alcohols and sec-octadecyl alcohols, benzoic acid esters of a mixture of sec-nonadecyl alcohols, sec-eicosyl alcohols, sec-heneicosyl alcohols, sec-docosyl alcohols, sec-tricosyl alcohols, sec-tetracosyl alcohols, sec-pentacosyl alcohols, sec-hexacosyl alcohols, sec-heptacosyl alcohols, sec-octacosyl alcohols, sec-nonacosyl alcohols, sec-triacontyl alcohols, sec-hentriacontyl alcohols or sec-dotriacontyl alcohols, methyl caproate, ethyl caproate, isopropyl caproate, methyl caprylate, ethyl caprylate, isopropyl caprylate, methyl caprate, ethyl caprate, isopropyl caprate, methyl laurate, ethyl laurate, isopropyl laurate, methyl myristate, ethyl myristate, isopropyl myristate, methyl palmitate, ethyl palmitate, isopropyl palmitate, methyl stearate, ethyl stearate, isopropyl stearate, methyl oleate, ethyl oleate isopropyl oleate, methyl linoleate, ethyl linoleate isopropyl linoleate, methyl linolenate, ethyl linolenate isopropyl linolenate, methyl arachidate, ethyl arachidate, isopropyl arachidate, methyl behenate, ethyl behenate, isopropyl behenate and mixtures thereof.

In one embodiment of the present invention, the catalyst composition used in step (ii) comprises an ester as component (c) which is the same as the carboxylic acid ester being alkoxylated from step (i).

The peroxy acid that may be optionally used as component (d) in the catalyst composition of step (ii) of the process of the present invention, may be conveniently selected from percarboxylic acid, perhalic acid, hypohalous acid, percarbonic acid, perboric acid, perphosphoric acid, persulphuric acid and mixtures thereof.

Peroxy acid salts that may be conveniently used include ammonium, alkali metal and/or alkaline earth metal salts. Examples of alkali metals and alkaline earth metal salts that are preferred include sodium, potassium, calcium, magnesium and barium salts.

Examples of particularly preferred peroxy acid salts are ammonium, alkali metal and alkaline earth metal persulphates, in particular ammonium, sodium, potassium and barium persulphates. Ammonium persulphate (also known as ammonium peroxydisulphate, $(NH_4)_2S_2O_8$) is preferred. Such salts are commercially available.

As mentioned hereinabove, in a preferred embodiment of the present invention, the catalyst composition used in step (ii) of the process of the present invention is in the form of a visually homogeneous, liquid suspension or a homogeneous paste.

In one embodiment, the catalyst composition used in step (ii) of the process of the present invention may be used as a freshly-prepared finely milled (for example, in a colloid mill, in a ball-mill or with an ultrasonic homogeniser, such as the "Labsonic P" of 400 W max, manufactured by Sartorius AG, Goettingen, Germany) mixture of components (a) to (c) and optionally, (d).

For example, when said catalyst composition comprises components (a)-(d) and/or products of the reciprocal reactions of (a), (b), (c) and/or (d), then said catalyst composition of the present invention may be conveniently prepared by firstly admixing a peroxy acid and/or a salt thereof to the oxy-acid to give a peroxy-containing acidic solution comprising a peroxy acid and/or a peroxy salt in an amount in the range of from 0.02 to 20 wt. %, more preferably in the range of from 0.06 to 6 wt. %, and most preferably in the range of from 0.2 to 2 wt. %, based on the total weight of the peroxy acid and/or a salt thereof and the oxy-acid.

This peroxy-containing acidic solution is admixed slowly under vigorous stirring to a suspension of one or more alkaline earth metal salts of carboxylic and/or hydroxycarboxylic acids and/or hydrates of the former in an alcohol and/or an ester at a temperature typically in the range of from 283 to 368 K, preferably at temperatures below 313 K.

For example, in a preferred embodiment, a 0.55 wt. % solution of ammonium peroxydisulphate in concentrated (95-97%) sulphuric acid may be admixed with a suspension of calcium acetate monohydrate or calcium lactate under vigorous stirring at such a rate that the temperature does not rise above 313 K, even more preferably at a rate such that the temperature is below 303 K.

In a particularly preferred embodiment, a 0.55 wt. % solution of ammonium peroxydisulphate in concentrated (95-97%) sulphuric acid may be admixed with a suspension of calcium acetate monohydrate under vigorous stirring at such a rate that the temperature does not rise above 303 K, whereupon the suspension is subsequently treated with an ultrasonic mixing device at temperatures below 303 K for 1 minute.

In a particularly preferred embodiment of the present invention, said catalyst composition comprises (a) one or more alkaline earth metal salts of carboxylic and/or hydroxycarboxylic acids and/or hydrates of the former, (b) an oxy-acid selected from sulphuric acid and ortho-phosphoric acid, (c) an alcohol and/or an ester and (d) a peroxy acid and/or a salt thereof, and/or products of the reciprocal reactions of (a), (b), (c) and/or (d), being formed on homogenisation, the components (a) and (b) being present in concentrations in the range of from 10 to 65 wt. %, with respect to the total weight of the catalyst composition, as calculated from the proportions of components (a) to (d) employed in the catalyst preparation.

The catalyst composition for use in step (ii) of the process of the present invention may be used in a catalytically effective amount, i.e. an amount sufficient to promote the alkoxylation reaction or influence the alkylene oxide adduct distribution of the product. Although a specific quantity of catalyst is not critical to the process of the present invention, preference may be expressed for use of said catalyst composition in step (ii) an amount of at least 0.05 wt. %, while an amount in the range of from 0.2 to 5 wt. % is more preferred and an amount in the range of from 0.5 to 2 wt. % is most preferred for typical embodiments. These percentages are in terms of the weight of the catalyst composition in the process mixture relative to the total weight of product of step (i) after removal of the volatile components (e.g. solvent and/or excess of carboxylic acid) from that reaction mixture of step (i).

Substantially greater quantities of said catalyst composition may also be employed in step (ii), e.g. up to 10 wt. %, or more. As a rule, the higher the desired average alkylene oxide adduct number of the alkoxylate product and the higher the desired rate of reaction, then the greater the required quantity of catalyst.

In the alkoxylation process of step (ii) of the process of the present invention, the alkylene oxide (epoxide) reactants may be conveniently selected from one or more vicinal alkylene oxides, particularly the lower alkylene oxides and more particularly those in the $C_2$ to $C_4$ range. In general, the alkylene oxides may be represented by the formula,

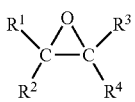

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide and propylene oxide. Alkylene oxide reactants consisting essentially of ethylene oxide are considered most preferred from the standpoint of commercial opportunities for the practice of alkoxylation processes, and also from the standpoint of the preparation of products having narrow-range ethylene oxide adduct distributions.

Preferred carboxylic acid esters formed in step (i), for subsequent reaction in step (ii) of the process of the present invention include esters of formic acid, acetic acid, propionic acid, butyric acid, isobutyric acid, pentanoic acid, caproic acid and optionally substituted benzoic acids, including those in which one or more hydrogen atoms of the benzene ring are substituted by one or more inert functional groups, that is to say, functional groups that will not interfere in the reaction of step (ii). Examples of inert functional groups that may be present include chlorine and bromine atoms, nitro groups and alkoxy groups such as methoxy groups.

More preferred carboxylic acid esters formed in step (i), for subsequent reaction in step (ii) of the process of the present invention are acetic acid esters, isobutyric acid esters, benzoic acid esters and fatty acid esters.

Examples of said fatty acid esters include esters of caproic acid, caprylic acid, capric acid, lauric acid, myristic acid, palmitic acid, stearic acid, oleic acid, linoleic acid, linolenic acid, arachidic acid, behenic acid and mixtures thereof.

Carboxylic acid esters, and in particular fatty acid esters, that may be conveniently employed in the alkoxylation process of step (ii) of the process of the present invention, after formation in step (i) thereof, include, for example, sec-butyl esters, sec-amyl esters and tert-amyl esters, sec-decyl esters such as 2-decyl, 3-decyl, 4-decyl and 5-decyl esters and their mixtures, sec-undecyl esters, sec-dodecyl esters, such as 2-undecyl, 3-undecyl, 4-undecyl, 5-undecyl, 2-dodecyl, 3-dodecyl, 4-dodecyl, 5-dodecyl and 6-dodecyl esters and their mixtures, sec-tridecyl esters and sec-tetradecyl esters, such as 2-tridecyl, 3-tridecyl, 4-tridecyl, 5-tridecyl, 6-tridecyl, 2-tetradecyl, 3-tetradecyl, 4-tetradecyl, 5-tetradecyl, 6-tetradecyl, 7-tetradecyl esters and their mixtures, sec-pentadecyl esters, sec-hexadecyl esters, sec-heptadecyl esters, sec-octadecyl esters and their mixtures, sec-nonadecyl esters, sec-eicosyl esters, sec-heneicosyl esters, sec-docosyl esters, sec-tricosyl esters, sec-tetracosyl esters, sec-pentacosyl esters, sec-hexacosyl esters, sec-heptacosyl esters, sec-octacosyl esters, sec-nonacosyl esters, sec-triacontyl esters, sec-hentriacontyl esters, sec-dotriacontyl esters and their mixtures.

Preferred carboxylic acid esters that may be conveniently employed in the alkoxylation process of step (ii) of the process of the present invention, after formation in step (i) thereof, include, sec-butyl, sec-amyl, tert-amyl, sec-decyl such as 2-decyl, 3-decyl, 4-decyl and 5-decyl, sec-undecyl, sec-dodecyl such as 2-undecyl, 3-undecyl, 4-undecyl, 5-undecyl, 2-dodecyl, 3-dodecyl, 4-dodecyl, 5-dodecyl and 6-dodecyl, sec-tridecyl, sec-tetradecyl such as 2-tridecyl, 3-tridecyl, 4-tridecyl, 5-tridecyl, 6-tridecyl, 2-tetradecyl, 3-tetradecyl, 4-tetradecyl, 5-tetradecyl, 6-tetradecyl, 7-tetradecyl, sec-pentadecyl, sec-hexadecyl, sec-heptadecyl, sec-octadecyl, sec-nonadecyl, sec-eicosyl, sec-heneicosyl, sec-docosyl, sec-tricosyl, sec-tetracosyl, sec-pentacosyl, sec-hexacosyl, sec-heptacosyl, sec-octacosyl, sec-nonacosyl, sec-triacontyl, sec-hentriacontyl, and sec-dotriacontyl acetates, and mixtures thereof.

Another class of preferred carboxylic acid esters that may be conveniently employed in the alkoxylation process of step (ii) of the process of the present invention, after formation in step (i) thereof, include, sec-butyl, sec-amyl, tert-amyl, sec-decyl such as 2-decyl, 3-decyl, 4-decyl and 5-decyl, sec-undecyl, sec-dodecyl such as 2-undecyl, 3-undecyl, 4-undecyl, 5-undecyl, 2-dodecyl, 3-dodecyl, 4-dodecyl, 5-dodecyl and 6-dodecyl, sec-tridecyl, sec-tetradecyl such as 2-tridecyl, 3-tridecyl, 4-tridecyl, 5-tridecyl, 6-tridecyl, 2-tetradecyl, 3-tetradecyl, 4-tetradecyl, 5-tetradecyl, 6-tetradecyl, 7-tetradecyl, sec-pentadecyl, sec-hexadecyl, sec-heptadecyl, sec-octadecyl, sec-nonadecyl, sec-eicosyl, sec-heneicosyl, sec-docosyl, sec-tricosyl, sec-tetracosyl, sec-pentacosyl, sec-hexacosyl, sec-heptacosyl, sec-octacosyl, sec-nonacosyl, sec-triacontyl, sec-hentriacontyl, and sec-dotriacontyl isobutyrates, and mixtures thereof.

Yet another class of preferred carboxylic acid esters that may be conveniently employed in the alkoxylation process of step (ii) of the process of the present invention, after formation in step (i) thereof, include, sec-butyl, sec-amyl, tert-amyl, sec-decyl such as 2-decyl, 3-decyl, 4-decyl and 5-decyl, sec-undecyl, sec-dodecyl such as 2-undecyl, 3-undecyl, 4-undecyl, 5-undecyl, 2-dodecyl, 3-dodecyl, 4-dodecyl, 5-dodecyl and 6-dodecyl, sec-tridecyl, sec-tetradecyl such as 2-tridecyl, 3-tridecyl, 4-tridecyl, 5-tridecyl, 6-tridecyl, 2-tetradecyl, 3-tetradecyl, 4-tetradecyl, 5-tetradecyl, 6-tetradecyl, 7-tetradecyl, sec-pentadecyl, sec-hexadecyl, sec-heptadecyl, sec-octadecyl, sec-nonadecyl, sec-eicosyl, sec-heneicosyl, sec-docosyl, sec-tricosyl, sec-tetracosyl, sec-pentacosyl, sec-hexacosyl, sec-heptacosyl, sec-octacosyl, sec-nonacosyl, sec-triacontyl, sec-hentriacontyl, and sec-dotriacontyl benzoates, and mixtures thereof.

In terms of processing procedures, the alkoxylation reaction of step (ii) of the process of the present invention may be conducted in a generally conventional manner. For example, the catalyst composition used in step (ii) together with the liquid carboxylic acid ester reactant from step (i) may be contacted, preferably under agitation, with alkylene oxide reactant, which is typically introduced in gaseous form, at least for the lower alkylene oxides.

Additional liquid carboxylic acid ester reactant from step (i) can optionally be added anytime before the addition of the alkylene oxide reactant. Thus, a concentrated catalyst reaction mixture can be made and a portion can be used as necessary.

In preferred embodiments of the process of the present invention, the alkylene oxide reactant is ethylene oxide or propylene oxide or a mixture of ethylene oxide and propylene oxide.

In a particularly preferred embodiment, ethylene oxide is contacted and reacted in step (ii) with a carboxylic acid ester from step (i), preferably a fatty acid ester, in the presence of a catalytically effective amount of an alkoxylation catalyst composition as described herein. Additional liquid carboxylic acid ester reactant from step (i) can be optionally added at any time during the process.

In another embodiment of the present invention, the alkoxylation process of step (ii) may be conducted according to the method described in WO-A-2005/115964, which is incorporated by reference herein.

That is to say, in one embodiment, the alkoxylation process of step (ii) of the process of the present invention comprises introducing the alkylene oxide reactant into a reactor filled with the carboxylic acid ester reactant from step (i) in the presence of a catalyst composition as described herein, wherein the reactor is filled with a portion (x') of a pre-designed total quantity (X) of the carboxylic acid ester reactant from step (i) to be subjected to alkoxylation and with a total pre-designed quantity (Y) of said catalyst composition, whereupon another portion (z') of the pre-designed total quantity (Z) of alkylene oxide reactant is fed to the reactor to activate said catalyst composition and induce a reaction and after the introduced quantity (z') of alkylene oxide reactant has been converted entirely or partly, the carboxylic acid ester reactant feed is supplemented with additional carboxylic ester from step (i) to the pre-designed quantity (X) and alkylene oxide reactant is continued to be fed until the pre-designed quantity (Z) has been introduced, preferably, the portion (x') of the carboxylic acid ester reactant from step (i) introduced in the initial phase of the synthesis is as small as possible relative to the total pre-designed carboxylic acid ester reactant feed (X) from step (i), that is, its quantity is around the minimum feed specified for a given reactor, that is, when the value of the quotient x'/X is as small as possible.

While the above procedures describe batch modes of operation, the process of the present invention is equally applicable to a continuous process.

Overall, the two reactants in step (ii) are utilised in quantities which are predetermined to yield an alkoxylate product of the desired mean or average adduct number. The average adduct number of the product is not critical to the process of the present invention. Such products commonly have an average adduct number in the range of from less than 1 to 30, or greater.

In general terms, suitable and preferred process temperatures and pressures for purposes of the alkoxylation process of step (ii) of the process of the present invention are the same as in conventional alkoxylation reactions between the same reactants, employing conventional catalysts. A temperature of at least 90° C., particularly at least 120° C., and most particularly at least 130° C., is typically preferred from the standpoint of the rate of reaction, while a temperature of less than 250° C., particularly of less than 210° C., and most particularly of less than 190° C., is typically desirable to minimise degradation of the product. As is known in the art, the process temperature can be optimised for given reactants, taking such factors into account.

Super-atmospheric pressures, e.g. pressures in the range of from 0.7 and 1 MPa gauge (about 10 and about 150 psig), are preferred in step (ii), which pressures are typically sufficient to maintain the carboxylic acid ester reactants from step (i) substantially in the liquid state during the reaction in step (ii).

When the carboxylic acid ester reactant from step (i) is a liquid and the alkylene oxide reactant in step (ii) is a vapour, alkoxylation in step (ii) is then suitably conducted by introducing alkylene oxide into a pressure reactor containing the liquid carboxylic acid ester reactant and the catalyst composition. For considerations of process safety the alkylene oxide reactant is preferably diluted with an inert gas such as nitrogen, for instance, to a vapour phase concentration of about 50 vol. percent or less. The reaction of step (ii) can, however, be safely accomplished at greater alkylene oxide concentrations, greater total pressure and greater partial pressure of alkylene oxide if suitable precautions, known in the art, are taken to manage the risks of explosion.

The time required to complete an alkoxylation process in step (ii) is dependent both upon the degree of alkoxylation that is desired (i.e. upon the average alkylene oxide adduct number of the product) as well as upon the rate of the alkoxylation reaction (which is, in turn, dependent upon temperature, catalyst quantity and nature of the reactants). A typical reaction time for preferred embodiments, particularly for when the alkylene oxide is gaseous, is less than 12 hours. When ethylene oxide is used as the alkylene oxide, the typical reaction time is less than 5 hours. When propylene oxide is used as the alkylene oxide, the typical reaction time is less than 8 hours.

After the alkoxylation reaction of step (ii) has been completed, the product is preferably cooled. If desired, the catalyst composition can be removed from the product. In embodiments of the present invention wherein the one or more acylated secondary alcohol alkoxylates from step (ii) are to undergo a further optional step, (iii), in order to hydrolyse or transesterify said the one or more acylated secondary alcohol alkoxylates to form one or more secondary alcohol alkoxylates, then catalyst removal is not necessary prior to step (iii) being carried out.

Catalyst residues may be removed from the one or more acylated secondary alcohol alkoxylates from step (ii), for example, by filtration, precipitation or extraction. A number of specific chemical and physical treatment methods have been found to facilitate removal of catalyst residues from the liquid product of step (ii). Such treatments include contact of the alkoxylation product with strong acids such as phosphoric and/or oxalic acids or with solid organic acids such as those sold under the trade designations "NAFION" H+ (E.I. du Pont de Nemours & Co., Inc.) and "AMBERLITE" IR 120H (Rohm & Haas Co.) from Sigma-Aldrich; contact with alkali metal carbonates and bicarbonates; contact with zeolites such as type Y zeolite or mordenite; or contact with certain clays. Typically, such treatments are followed by filtration or precipitation of the solids from the product. In many cases filtration, precipitation or centrifugation is most efficient at elevated temperature.

Preferred acylated secondary alcohol alkoxylate compositions which may be prepared by steps (i) and (ii) of the present process for optional subsequent hydrolysis or transesterification (also known as transacylation) in step (iii), are those comprising one or more acylated secondary alcohol alkoxylates, in particular alkoxylated fatty esters, having the formula (I):

$$R^1-C(O)-(OA)_n-OR^2 \qquad (I)$$

wherein $R^1$ is a straight chain or branched alkyl group having from 1 to 30 carbon atoms, an optionally substituted cycloalkyl group having 5 to 30 carbon atoms or an optionally substituted aryl group having 6 to 30 carbon atoms, OA represents one or more oxyalkylene moieties which may be the same or different, n is an integer in the range of from 0 to 70 and $R^2$ is a straight chain or branched alkyl group having from 4 to 32 carbon atoms, an optionally substituted cycloalkyl group of 5 to 32 carbon atoms or an optionally substituted bicycloalkyl group of 7 to 32 carbon atoms.

Particularly preferred acylated secondary alcohol alkoxylates, including fatty ester alkoxylates, which may be prepared by steps (i) and (ii) of the present process for optional subsequent hydrolysis in step (iii), are those wherein $R^1$ is a straight chain or branched alkyl group having from 1 to 22 carbon atoms or an optionally substituted phenyl group, OA is selected independently from oxyethylene and oxypropylene moieties, n is an integer in the range of from 1 to 30 and $R^2$ is a straight chain or branched alkyl group having from 4 to 32 carbon atoms.

Acylated secondary alcohol alkoxylates, which may be prepared by steps (i) and (ii) of the present process for subsequent optional hydrolysis in step (iii), and which are especially preferred for the purpose of detergent applications are compounds of formula (I) wherein $R^1$ is an optionally substituted phenyl group, preferably a phenyl group, hydrogen or an alkyl group having in the range of from 1 to 22 carbon atoms, preferably 1 carbon atom, OA is selected independently from oxyethylene and oxypropylene moieties, n is an integer in the range of from 1 to 30 and $R^2$ is a straight chain or branched alkyl group having in the range of from 4 to 32 carbon atoms.

In one embodiment of the present invention, preferred acylated secondary alcohol alkoxylates are acetic ester alkoxylate compositions, that is to say, compounds of formula (I) wherein $R^1$ is a methyl group, OA is selected independently from oxyethylene and oxypropylene moieties, n is an integer in the range of from 1 to 30 and $R^2$ is a straight chain or branched alkyl group having in the range of from 4 to 32 carbon atoms.

Fatty acid ester alkoxylates, which may be prepared by steps (i) and (ii) of the present process for subsequent optional hydrolysis in step (iii), and which are especially preferred for the purpose of detergent applications are compounds of formula (I), wherein $R^1$ is an alkyl group having from 6 to 22 carbon atoms, preferably from 9 to 15 carbon atoms, OA is selected independently from oxyethylene and oxypropylene moieties, n is an integer in the range of from 1 to 30 and $R^2$ is a straight chain or branched alkyl group having from 4 to 32 carbon atoms, preferably from 4 to 6 carbon atoms.

In formula (I), the different OA groups can be distributed randomly along the alkoxide chain or be present as block (co)-polymers.

An optional step (iii) comprising hydrolysis or transesterification (also known as transacylation) may be performed in order to liberate one or more secondary alcohol alkoxylates from the one or more acylated secondary alcohol alkoxylates from step (ii).

Step (iii) may be performed under conditions well known in the art for hydrolysis and transesterification reactions. Temperatures that may be conveniently used for such a step are those in the range of from 0 to 200° C., preferably in the range of from 50 to 150° C. Pressures that may conveniently be employed are generally atmospheric, although super-atmospheric or sub-atmospheric pressures may also be employed. Generally acid or basic catalysts are used in <10% (mol/mol) quantities (on acylated secondary alcohol alkoxylate) to accelerate the rate of the transesterification reaction. Examples of acidic catalysts are p-toluenesulphonic acid, sulphuric acid and ortho-phosphoric acid and an example of a basic catalyst is potassium tert-butoxide. Alcohols that may be conveniently used for transesterification of the one or more acylated secondary alcohol alkoxylates from step (ii) include methanol, ethanol, isopropyl alcohol, and tert-butyl alcohol.

The secondary alcohol alkoxylates prepared by step (iii) of the process of the present invention may be sulphated in order to form secondary alcohol alkoxy sulphates.

Accordingly, in another embodiment of the present invention there is further provided a process for making secondary alcohol alkoxy sulphates comprising sulphating the secondary alcohol alkoxylates produced as hereinbefore described.

That is to say, the present invention further provides a process for making secondary alcohol alkoxy sulphates comprising the steps of:—
preparing secondary alcohol alkoxylates by the afore-mentioned process; and
sulphating the secondary alcohol alkoxylates.

Sulphating agents that may be conveniently used include including sulphur trioxide, complexes of sulphur trioxide with (Lewis) bases, such as the sulphur trioxide pyridine complex and the sulphur trioxide trimethylamine complex, chlorosulphonic acid and sulphamic acid.

The sulphation reaction may be carried out at a temperature preferably not above 80° C. The sulphation may be carried out at temperature as low as about −20° C., however higher temperatures are more economical. For example, the sulphation may be conveniently carried out at a temperature in the range of from 20 to 70° C., preferably in the range of from 20 to 60° C., and more preferably in the range of from 20 to 50° C. Sulphur trioxide is the most economical sulphating agent.

The secondary alcohol alkoxylates may be reacted with a gas mixture which in addition to at least one inert gas contains in the range of from 1 to 8 percent by volume (vol. %), relative to the gas mixture, of gaseous sulphur trioxide, preferably in the range of from 1.5 to 5 vol. %. In principle, it is possible to use gas mixtures having less than 1 vol. % of sulphur trioxide but the space-time yield is then decreased unnecessarily. Inert gas mixtures having more than 8 vol. % of sulphur trioxide in general may lead to difficulties due to uneven sulphation, lack of consistent temperature and increasing formation of undesired by-products. Although other inert gases are also suitable, air or nitrogen are preferred, as a rule because of easy availability.

The reaction of the secondary alcohol alkoxylate with the sulphur trioxide containing inert gas may be carried out in falling film reactors. Such reactors utilise a liquid film trickling in a thin layer on a cooled wall which is brought into contact in a continuous current with the gas. Kettle cascades, for example, would be suitable as possible reactors. Other reactors include stirred tank reactors, which may be employed if the sulphation is carried out using sulphamic acid or a complex of sulphur trioxide and a (Lewis) base, such as the sulphur trioxide pyridine complex or the sulphur trioxide trimethylamine complex. These sulphation agents would allow an increased residence time of sulphation without the risk of ethoxylate chain degradation and olefin elimination by (Lewis) acid catalysis.

The molar ratio of sulphur trioxide to alkoxylate may be in the range of 1.4 to 1 or less including in the range of from 0.8 to 1 mole of sulphur trioxide used per mole of OH groups in the alkoxylate and latter ratio is preferred. Sulphur trioxide may be used to sulphate the alkoxylates and the temperature may range from −20 to 50° C., preferably from 5 to 40° C., and the pressure may be in the range of from 100 to 500 kPa abs. The reaction may be carried out continuously or discontinuously. The residence time for sulphation may range from 0.5 seconds to 10 hours, but is preferably from 0.5 seconds to 20 minutes.

The sulphation may be carried out using chlorosulphonic acid at a temperature in the range of from −20 to 50° C., preferably from 0 to 30° C. The mole ratio between the alkoxylate and the chlorosulphonic acid may range from 1:0.8 to 1:1.2, preferably 1:0.8 to 1:1. The reaction may be carried out continuously or discontinuously for a time between fractions of seconds (i.e., 0.5 seconds) to 20 minutes.

Unless they are only used to generate gaseous sulphur trioxide to be used in sulphation, the use of sulphuric acid and oleum should be omitted. Subjecting any alkoxylate, for example, an ethoxylate, to these reagents leads to ether bond breaking—expulsion of 1,4-dioxane (back-biting)—and finally conversion of secondary alcohol to an internal olefin.

In primary alcohol ethoxy sulphate production the neutralisation of the half-ester of sulphuric acid should be done as swiftly as possible, since otherwise elimination of sulphur trioxide will occur. This may lead to ethoxylate chain degradation with concomitant formation of 1,4-dioxane and shorter chain ethoxylates or finally primary alcohols or olefins, depending on the reaction conditions. In the case of secondary alcohol ethoxylates, and particularly those with a low average number of EO units, i.e. the low mol secondary alcohol ethoxylates as prepared herein, an excess of the Lewis acid sulphur trioxide should be avoided at all times since otherwise internal olefins, 1,4-dioxane, sulphur trioxide or sulphuric acid will become important by-products, depending on the reaction conditions. This prerequisite is anticipated to limit the sulphation conversion level of secondary alcohol ethoxylates or an alternative to this problem inherent to the sulphation of low-mol secondary alcohol ethoxylates under (Lewis) acid conditions has to be identified.

Following sulphation, the liquid reaction mixture may be neutralised using an aqueous alkali metal hydroxide, such as sodium hydroxide or potassium hydroxide, an aqueous alkaline earth metal hydroxide, such as magnesium hydroxide or calcium hydroxide, or bases such as ammonium hydroxide, substituted ammonium hydroxide, sodium carbonate or potassium hydrogen carbonate. The neutralisation procedure may be carried out over a wide range of temperatures and pressures. For example, the neutralisation procedure may be carried out at a temperature in the range of from 0 to 65° C. and a pressure in the range of from 100 to 200 kPa abs. The neutralisation time may be in the range of from 0.5 hours to 1 hour but shorter and longer times may be used where appropriate.

The present invention will now be illustrated by the following examples which are not intended to limit the scope of the invention in any way.

EXAMPLES (i) Catalyst Preparation
Catalyst 1
Calcium acetate monohydrate (5.5 g) (as 99% grade available from Aldrich) was added to 23 ml isopropyl alcohol (IPA, as PA-grade available from Merck) at ambient temperature and atmospheric pressure. About 0.8 ml of concentrated sulphuric acid (95-97% available from Merck), was dosed to the mixture under vigorous stirring with a magnetic bar at such a rate that the temperature remains below 40° C. After that the mixture, a milky suspension, was stirred for another 30 minutes and was thereafter used as such as an alkoxide-insertion catalyst ("Catalyst 1").

Catalyst 2
Calcium acetate monohydrate (5.5 g) (as 99% grade available from Aldrich) was added to 23 ml isopropyl alcohol (IPA, as PA-grade available from Merck) at ambient temperature and atmospheric pressure. About 0.8 ml of concentrated sulphuric acid (95-97% available from Merck) to which 0.55 wt. % ammonium persulphate (available from Aldrich) has been added, was dosed to the mixture under vigorous stirring with a magnetic bar at such a rate that the temperature remains below 40° C. After that the mixture, a milky suspension, was stirred for another 30 minutes and was thereafter used as such as an alkoxide-insertion catalyst ("Catalyst 2").

(ii) Acetoxylation
Although acetoxylation has been carried out in Examples 1 and 2 on an α-olefin rather than a corresponding C12 internal olefin, the person skilled in the art will appreciate that similar ester products would have been produced using such an internal olefin.

Example 1

Acetoxylation of 1-Dodecene

1-Dodecene (77.2 g, 0.46 mol) and 55.4 g acetic acid were placed in a round-bottomed flask. The mixture was heated at 120° C. in an oil bath. The mixture became clear and subsequently 0.4 ml $H_2SO_4$ was added. The mixture turned rapidly into a brown solution. The mixture was allowed to react for 33 hours. After cooling to room temperature the mixture was extracted with water to remove the acetic acid and the catalyst. The organic layer was analysed by GC and NMR (see Table 1 for NMR data). These analyses showed that the mixture consisted of 35% wt./wt. ester (mainly 2-dodecyl acetate and a minor amount of 3-dodecyl acetate) and 65% wt./wt. unreacted and double-bond isomerised 1-dodecene. This mixture was used as such, without any further purification, for the ethoxylation experiment described in Example 4.

TABLE 1

NMR Data for 2-Dodecyl Acetate

| | $^1$H-NMR (300 MHz, $CDCl_3$) | | $^{13}$C-NMR (300 MHz, $CDCl_3$) | |
|---|---|---|---|---|
| Position | δ (in ppm) | | Position | δ (in ppm) |
| A | 0.9 (3H, t) | | a | 14.0 |
| b-i | 1.3 (16H, m) | | b | 22.9 |
| | | | c | 32.2 |
| | | | d-h | 29.6-29.9 |
| | | | i | 25.7 |
| J | 1.6 (2H, m) | | j | 36.2 |
| K | 4.9 (1H, m) | | k | 71.4 |
| L | 1.3 (3H, d) | | l | 20.2 |
| — | — | | m | 171.0 |
| N | 2.0 (3H, s) | | n | 21.5 |

Example 2

Acetoxylation of 1-Dodecene

A 500-ml round-bottomed flask was charged with 120.8 g acetic acid (2 mol), 1.55 g $FeCl_3$ (9.5 mmol), 1.45 g triflic acid, CF$_3$SO$_3$H, (9.7 mmol) and 160.0 g 1-dodecene (0.95 mol), in that order. The chemicals used were purchased from Aldrich, except for glacial acetic acid which was obtained from Merck. The mixture was stirred at 80° C. in an oil bath for a period of 48 hours. The temperature was then raised to 100° C. and the reaction was allowed to continue for another 55 hours. Samples were taken during the reaction and the conversion was monitored by GC. After a total reaction time of 103 hours the mixture was cooled to room temperature and it was extracted 3 times with water to remove the unreacted acetic acid and the catalyst. A brown organic layer resulted. GC and NMR analysis showed that the mixture consisted of 33% wt./wt. 2-dodecyl acetate, 4% wt./wt. 3-dodecyl acetate and ~57% wt./wt. olefins (1-C$_{12}$═ and isomerised C$_{12}$═) and ~2% wt./wt. chlorododecane.

This mixture was distilled under reduced pressure (at 2 mbar during 2 hours at 150° C.) to remove the unreacted olefins as much as possible. The residue consisted of 60% wt./wt. 2-dodecyl acetate, 6% wt./wt. 3-dodecyl acetate and ~26% wt./wt. C$_{12}$-olefins.

(iii) Alkoxylation

Although alkoxylation has been carried out below using the ester product of Example 1, the person skilled in the art will appreciate that the alkoxylation reaction below can be carried out in an identical manner when the same ester product has been produced using the corresponding internal olefin.

Example 3

Propoxylation of 1-Dodecyl Acetate

A pressure tube sold under the trade designation "Ace" from Ace Glass Inc. was filled with 10 g dodecyl acetate (available from Aldrich), 0.2 g Catalyst 1 and 0.5 ml propylene oxide was stirred during 24 hours (3×8 hours) at 180° C. using an oil bath. Analysis by $^1$H-NMR indicated that about 35% of the propylene oxide (PO) had been converted to the PO insertion product. The presence of a multiplet at δ=5.0 ppm indicated the formation of a 2-acetoxypropylether and insertion of the propylene oxide in the ester bond.

Example 4

Ethoxylation of the Product of Example 1, the Acetoxylation Product of 1-Dodecene The product mixture from Example 1 was used as such, without any further purification, for the ethoxylation experiment described below.

40 g of the afore-mentioned product mixture from Example 1 and 0.82 g catalyst suspension (Catalyst 1) were added to a 120 ml autoclave (stainless steel). After closing, the autoclave was pressurised 3 times with nitrogen (4-5 barg) to purge the gas cap and it was heated to 130° C. At 130° C. the autoclave was purged with nitrogen (10-15 liter/min) for 30 minutes to dry the contents. The autoclave was then pressurised with 5 barg nitrogen and it was further heated to 165° C.

At 165° C., ethylene oxide (10-25 barg (EO/N$_2$<1 v/v)) was added in portions with the use of a high pressure syringe pump available from Teledyne Isco, Inc. For safety reasons, the amount of each EO-addition should not give a higher concentration than 50% v/v in nitrogen (generally each portion added consisted of 2-3 g of ethylene oxide). After addition of the first portion of ethylene oxide a short induction period of ca. 5 minutes was observed. Then the reaction started and the autoclave-pressure decreased quickly. When the pressure decrease levelled off (after 15-20 minutes), the next portion of ethylene oxide was added. The additions were repeated until the desired total amount of ethylene oxide (39.0 g) was reached.

When all ethylene oxide was added, 30 minutes extra reaction time was allowed to let the remaining EO react away. The autoclave was then cooled down to 80° C. and at this temperature the autoclave content was purged with nitrogen for 20 minutes to remove the last traces of dissolved free ethylene oxide before opening the autoclave. The temperature was then decreased to room temperature to enable a safe discharge of the product mixture.

Most of the mixture remained unchanged (brown liquid), however, a small part (estimated to be 5-10% of the total product) turned into an off-white sticky solid. According to the mass balance and to GC of the product mixture some ethylene oxide (EO) had reacted. The off-white sticky solid was confirmed to be an EO-insertion product of sec-dodecyl acetate by $^1$H-NMR (CDCl$_3$, 300 MHz), as it showed the characteristic signal of —CH$_2$— adjacent to —O(C═O)CH$_3$ at 4.2 ppm (position A in FIG. 1). This structure has been confirmed by LC-MS analysis.

Figure 1: Product of EO-Insertion in Sec-Dodecyl Acetate

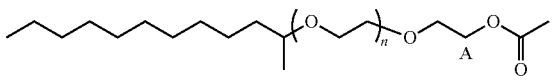

What is claimed is:

1. A process for the preparation of acylated secondary alcohol alkoxylates, said process comprising:—
   (i) reacting an internal olefin with a carboxylic acid in the presence of a catalyst composition to form a carboxylic acid ester;
   (ii) reacting said carboxylic acid ester from step (i) with an alkylene oxide reactant, in the presence of a catalytically effective amount of a catalyst composition comprising:
      (a) an alkaline earth metal salt of a carboxylic or hydroxy-carboxylic acid or a hydrate of the former;
      (b) an oxy-acid selected from sulphuric acid and ortho-phosphoric acid;
      (c) an alcohol or an ester;
      or products of the reciprocal reactions of (a), (b) and/or (c) in order to form an acylated secondary alcohol alkoxylate.

2. A process according to claim 1, wherein the catalyst composition of step (ii) comprises:
   (a) an alkaline earth metal salt of a carboxylic or hydroxy-carboxylic acid or a hydrate of the former;
   (b) an oxy-acid selected from sulphuric acid and ortho-phosphoric acid;
   (c) an alcohol or an ester;
   (d) a peroxy acid or a salt thereof;
   and/or products of the reciprocal reactions of (a), (b), (c) or (d).

3. A process according to claim 2, wherein the peroxy acid in the catalyst composition of step (ii) is selected from the group consisting of from percarboxylic acid, perhalic acid, hypohalous acid, percarbonic acid, perboric acid, perphosphoric acid and persulphuric acid or the peroxy acid salt in the catalyst composition of step (ii) is selected from the group consisting of from ammonium, alkali metal and alkaline earth metal salts.

4. A process according to claim 1, wherein the alkaline earth metal salts (a) in the catalyst composition of step (ii) is selected from calcium salts of carboxylic or hydroxycarboxylic acids and/or hydrates of the former.

5. A process according to claim 1, wherein the catalyst composition of step (i) comprises:
(a) at least one metal compound, wherein said metal is selected from the group consisting of from iron, cobalt and nickel; and
(b) an acidic compound.

6. A process according to claim 5, wherein the acidic compound is selected from a Brønsted acid or a metal salt of trifluoromethanesulphonic acid.

7. A process according to claim 1, wherein the internal olefin is selected from olefins having in the range of from 8 to 32 carbon atoms.

8. A process according to claim 1, wherein the alkylene oxide reactant is selected from ethylene oxide, propylene oxide or butylene oxide.

9. A process for making secondary alcohol alkoxylate comprising the steps of:
preparing an acylated secondary alcohol alkoxylate by the process of claim 1; and
hydrolysing or transesterifying said acylated secondary alcohol alkoxyate to form said secondary alcohol alkoxylate.

10. A process for making secondary alcohol alkoxy sulfates comprising the steps of:
preparing secondary alcohol alkoxylates by the process of claim 9; and
sulfating the secondary alcohol alkoxylates.

11. A process according claim 7, wherein the internal olefin reacted in step (i) is an olefin having 10 carbon atoms.

12. A process according claim 1, wherein carboxylic acid reacted in step (i) is acetic acid.

13. A process according claim 1, wherein alkylene oxide reacted in step (ii) is ethylene oxide.

14. A process according claim 1, wherein the catalyst composition of step (ii) comprises calcium acetate monohydrate as the alkaline earth metal salt of a carboxylic and/or hydroxycarboxylic acid or a hydrate of the former.

15. A process according claim 1, wherein the catalyst composition of step (ii) comprises suphuric acid as the oxy-acid.

16. A process according claim 1, wherein the alcohol and/or ester in the catalyst composition of step (ii) is isopropyl alcohol.

17. A process according claim 2, wherein the catalyst composition of step (ii) comprises ammonium persulphate as the peroxy acid or a salt thereof.

\* \* \* \* \*